(12) United States Patent
Jolivet et al.

(10) Patent No.: US 11,896,042 B2
(45) Date of Patent: Feb. 13, 2024

(54) RIBONUCLEOTIDE-RICH YEAST EXTRACT AND USE OF SAME FOR MASKING UNDESIRABLE FLAVOURS AND UNDESIRABLE AROMATIC NOTES

(71) Applicant: LESAFFRE ET COMPAGNIE, Paris (FR)

(72) Inventors: Hélène Jolivet, Vincennes (FR); Rudy Menin, Choisy le Roi (FR); Antoine Thomas, Paris (FR)

(73) Assignee: LESAFFRE ET COMPAGNIE, Paris (FR)

( * ) Notice: Subject to any disclaimer, the term of this patent is extended or adjusted under 35 U.S.C. 154(b) by 714 days.

(21) Appl. No.: 16/772,388

(22) PCT Filed: Nov. 12, 2018

(86) PCT No.: PCT/FR2018/052808
§ 371 (c)(1),
(2) Date: Jun. 12, 2020

(87) PCT Pub. No.: WO2019/115894
PCT Pub. Date: Jun. 20, 2019

(65) Prior Publication Data
US 2021/0076722 A1    Mar. 18, 2021

(30) Foreign Application Priority Data
Dec. 13, 2017  (FR) ...................... 17 62074

(51) Int. Cl.
| A23L 31/15 | (2016.01) |
| A23L 27/28 | (2016.01) |
| A23L 27/23 | (2016.01) |
| C12N 1/18  | (2006.01) |
| A23L 27/00 | (2016.01) |

(52) U.S. Cl.
CPC .............. *A23L 31/15* (2016.08); *A23L 27/23* (2016.08); *A23L 27/28* (2016.08); *A23L 27/86* (2016.08); *C12N 1/18* (2013.01)

(58) Field of Classification Search
None
See application file for complete search history.

(56) References Cited

U.S. PATENT DOCUMENTS

| 3,578,465 A      | 5/1971 | Van Der Zijden et al. |
| 2009/0148559 A1  | 6/2009 | Noordam et al.        |
| 2010/0183767 A1  | 7/2010 | Noordam et al.        |
| 2010/0303853 A1  | 12/2010 | Lejeune et al.       |
| 2014/0287097 A1  | 9/2014 | Batenburg et al.      |

FOREIGN PATENT DOCUMENTS

| EP | 0299078 A1     | 1/1989  |
| EP | 1080645 A1     | 3/2001  |
| FR | 2922728 A1     | 5/2009  |
| JP | 2000037170 A   | 2/2000  |
| JP | 2001269149 A * | 10/2001 |
| JP | 2001269149 A   | 10/2001 |
| JP | 2002-101846 A  | 4/2002  |
| JP | 2003169627 A   | 6/2003  |
| JP | 2009513108 A   | 4/2009  |
| JP | 2011501948 A   | 1/2011  |
| WO | 02/067959 A1   | 9/2002  |
| WO | 03/063613 A1   | 8/2003  |
| WO | 2004/067758 A2 | 8/2004  |
| WO | 2005/067734 A2 | 7/2005  |
| WO | 2008/068155 A1 | 6/2008  |

OTHER PUBLICATIONS

Charpentier C, Aussenac J, Charpentier M, Prome JC, Duteurtre B, Feuillat M., "Release of nucleotides and nucleosides during yeast autolysis: kinetics and potential impact on flavor." J Agric Food Chem. Apr. 20, 2005;53(8):3000-7. doi: 10.1021/jf040334y. PMID: 15826051.

Olsson, K., Carlsen, S., Semmler, A. et al., "Microbial production of next-generation stevia sweeteners." Microb Cell Fact 15, 207 (2016).

"Enzymatic Conversion of RNA from Yeast Extract to Guanosine Monophosphate (a flavoring agent)." Raja Makendran Nandan Raja Rajendran Department of Chemical and Biological Engineering Chalmers University of Technology, 2012.

Japanese Office Action dated Jun. 28, 2022 in corresponding Japanese Application No. 2020532667. (8 pages, including English translation).

International Search Report dated Mar. 15, 2019 in corresponding International Application No. PCT/FR2018/052808; 5 pages.

* cited by examiner

*Primary Examiner* — Jyoti Chawla
(74) *Attorney, Agent, or Firm* — Maier & Maier, PLLC

(57) ABSTRACT

A novel yeast extract having from 25 to 55 wt % 5'-ribonucleotides, including 5 to 20 wt % adenosine 5'-monophosphate (5'-AMP) and 5 to 20 wt % guanosine 5'-monophosphate (5'-GMP) in a 5'-AMP/5'-GMP ratio ranging from 0.85 to 1.25, the weight percentages being expressed in relation to the dry weight of the yeast extract. Also a process of using such an extract for the masking of bitter and sour tastes and of undesirable sweetener, protein and metallic notes in a product.

15 Claims, No Drawings

RIBONUCLEOTIDE-RICH YEAST EXTRACT AND USE OF SAME FOR MASKING UNDESIRABLE FLAVOURS AND UNDESIRABLE AROMATIC NOTES

FIELD

The invention relates to a novel 5'-ribonucleotide-rich yeast extract, the use of same for masking undesirable tastes and undesirable aromatic notes, and a process for masking undesirable tastes and undesirable aromatic notes in a product.

BACKGROUND

The perception of the taste of a food or substance is the product of a multitude of mechanisms, and is the result of taste, aroma and trigeminal sensations. A food's taste is also referred to as flavor. When a food is placed in the mouth, chewing releases volatile and non-volatile constituents, each of which has various consequences and effects on taste perception.

Non-volatile constituents, via receptor cells of the gustatory system, are responsible for taste. There are only five basic tastes, namely sourness, bitterness, sweetness, saltiness and umami.

Volatile constituents, in turn, are detected via receptor cells of the olfactory system, known as the retronasal pathway, and are responsible for aromas. Unlike tastes, there is a wide variety of aromas, which can be the result of several molecules.

Finally, both volatile and non-volatile components are detected by the nerve endings of the trigeminal nerve in the oral or nasal cavities. This detection produces a great diversity of sensations such as spiciness, astringency, heat or cold.

Therefore, the perception of the taste of foods or substances, through taste, aromas and trigeminal sensations, is a complex phenomenon.

Despite this complexity, it is sometimes necessary for certain applications, particularly food or pharmaceutical applications, to be able to mask tastes or the notes of certain aromas.

Consequently, manufacturers have for many years been developing solutions to enhance or mask certain tastes or aromas in products intended to be ingested. Indeed, certain tastes need to be enhanced without increasing the amounts of non-volatile compounds responsible for these tastes, while others should be masked, particularly undesirable tastes.

Concerning the enhancement of tastes, a good example is that of sweetness, for which it would be unacceptable in view of the health consequences to increase the sugar content of the food to enhance its perception. This is why alternative solutions have been developed to enhance the perception of the product without increasing its sugar content.

For example, the document EP 1 080 645 describes the use of an agent to enhance sweetness in food products containing sweeteners. In particular, the agent is a yeast extract containing 1 to 15 wt % sodium 5'-inosinate and/or sodium 5'-adenylate, 1 to 15 wt % sodium 5'-guanylate, 1 to 15 wt % sodium 5'-uridylate, 1 to 15 wt % sodium 5'-cytidylate and 1 to 20 wt % sodium glutamate, the weight percentages being given in relation to the weight of the yeast extract. A disadvantage of these yeast extracts is that they only potentiate sweetness, and therefore do not offer the possibility of masking particular tastes and/or aromatic notes in products for which said tastes or notes are harmful.

Certain constituents used for the manufacture or preservation of food products are not necessarily neutral and thus leave an undesirable taste or residual tastes in the mouth. Similarly, certain products themselves have tastes whose intensity may need to be reduced. Interestingly, yeast extracts can also be used to mask undesirable tastes or undesirable aromatic notes.

The document WO2003/063613 describes the use of a yeast extract in an artificial sweetener-based composition to mask sweetener notes. The yeast extract comprises free amino acids and 5'-ribonucleotides in a free amino acid/5'-ribonucleotide ratio below 3.5. The masking of sweetener notes is obtained with two particular yeast extracts, a first comprising 13 wt % 5'-ribonucleotides including 6.5 wt % 5'-IMP and 5'-GMP and a second comprising 8.5 wt % 5'-ribonucleotides including 4.3 wt % 5'-IMP and 5'-GMP. Although this extract may mask a note, it is only a sweetener note and it would be advantageous to have other masks available.

The document WO2005/0067734 describes a process for preparing a composition which can be used to increase and/or enhance the taste and aromas of foods, but also to mask the bitter taste generated by artificial sweeteners. The composition comprises yeast extracts having 15 to 55 wt % 5'-ribonucleotides, the percentages being given in relation to the non-NaCl dry weight of the composition. The description in this document also specifies that the amount of guanosine 5'-monophosphate (5'-GMP) in the composition is preferably greater than the sum of the amount of adenosine 5'-monophosphate (5'-AMP) and inosine 5'-monophosphate (5'-IMP) because 5'-GMP is more effective in improving taste perception than 5'-IMP.

Yeast extracts can also be used to mask metallic notes of certain salt substitutes. For example, the document WO2008/0068155 describes the use of yeast extracts comprising at least 30 wt % 5'-ribonucleotides to mask the metallic notes generated by salt substitutes in cereal products. This effect is obtained with 5'-ribonucleotide-rich yeast extracts comprising particularly at least 20 wt % 5'-GMP and 5'-IMP. The percentages are given in relation to the non-NaCl dry weight of the composition.

Concerning food applications, yeast extracts can therefore be used both to enhance tastes present in products and to mask undesirable notes. This dissimilarity in applications is explained notably by the complexity and diversity of the compounds contained in yeast extracts, thus making it particularly difficult to obtain novel extracts with specific properties. Similarly, as explained above, taste perception is governed by complex mechanisms involving several sensory systems and a wide variety of compounds. All this probably explains why, in order to mask undesirable tastes and undesirable aromatic notes, manufacturers only develop yeast extracts that produce one type of masking.

Therefore, there is a need to have novel yeast extracts capable of producing several types of masking without the need to modify their composition and without generating an undesirable taste in the products in which they are incorporated. Indeed, a product's flavor is the result of a subtle equation. Thus, to produce several types of masking with a single extract, without altering the perception of taste in the mouth, was far from obvious.

SUMMARY

It is therefore to the Applicant's credit to have succeeded, as the result of extensive research, in developing a particular yeast extract, said yeast extract having combined properties of masking undesirable tastes and undesirable aromatic notes that have never before been achieved. The yeast extracts developed thus have a very specific application in the manufacture of food, pharmaceutical or nutraceutical products or aromatic preparations.

The present invention thus relates to a novel yeast extract comprising from 25 to 55 wt % 5'-ribonucleotides, including 5 to 20 wt % adenosine 5'-monophosphate (5'-AMP) and 5 to 20 wt % guanosine 5'-monophosphate (5'-GMP) in a 5'-AMP/5'-GMP ratio ranging from 0.85 to 1.25, the weight percentages being expressed in relation to the dry weight of the yeast extract and calculated taking into account the disodium heptahydrate form of the 5'-ribonucleotides. The invention also relates to the use of such a yeast extract to mask bitter and sour tastes and undesirable sweetener, protein and metallic aromatic notes in a product.

DETAILED DESCRIPTION

Throughout the description, and by way of clarification, the weight percentages are always expressed in relation to the dry weight of the yeast extract, except when the context allows the contrary to be identified unambiguously.

Within the meaning of the present invention, the masking of a taste consists in reducing or completely eliminating the perception of a taste in a product, while the masking of an off-note consists in reducing or completely eliminating the perception of an aroma or an aromatic note.

The yeast extract according to the invention is particularly remarkable in that it masks both the bitter and sour tastes and the undesirable sweetener, protein and metallic aromatic notes in products without altering the overall perception of the taste of said products. Indeed, the yeast extract used according to the invention does not generate the broth notes, the aromatic notes of yeast or the umami taste (grouped under the expression "yeasty taste") generally characteristic of these extracts.

Within the meaning of the present invention, the term product refers both to food, pharmaceutical or nutraceutical products and to aromatic preparations which can be used in food, pharmaceutical or nutraceutical applications.

A food product within the meaning of the present invention may be considered as any substance providing nutrition for a living being, and particularly for a human being. The food product may therefore be in either solid or liquid form. By way of example, the food product may be a prepared dish, a jam, a fermented drink such as wine or beer, an energy drink or a protein drink for sport.

A pharmaceutical product within the meaning of the present invention refers to any pharmaceutical substance intended to be ingested by a human being, such as a drug.

Quite surprisingly, the inventors found that a yeast extract having from 25 to 55 wt % 5'-ribonucleotides, including a specific amount of 5'-AMP and 5'-GMP in a 5'-AMP/5'-GMP ratio of 0.85 to 1.25, when used in the preparation of products, masked bitter and sour tastes and undesirable sweetener, protein and metallic aromatic notes. This effect is notably achieved without the need to convert 5'-AMP to 5'-IMP as was commonly done in the prior art when using 5'-ribonucleotide-rich yeast extracts as a sweetener note masking agent.

In general, yeast extracts are known products. According to the invention, yeast extract means the soluble fraction obtained after enzymatic hydrolysis of yeast cells. Further, according to the invention, the yeast extract is preferably the soluble fraction obtained after autolysis of said yeast cells, in other words after enzymatic hydrolysis carried out only by endogenous yeast enzymes. Hydrolysis of the yeast cells can also be carried out by means of exogenous enzymes, in other words by adding additional enzymes such as proteases.

Preferably, the yeast extract is separated from the insoluble part of the yeast cells. The yeast extract thus separated from the insoluble part offers the advantage of better preservation without the appearance of aromatic notes due to oxidation of the membrane lipids of the insoluble part.

The yeast extract according to the invention may be obtained from any yeast. Preferably, the yeast strain used to prepare the extract according to the invention belongs to the genus *Saccharomyces, Kluyveromyces* or *Candida* (also known as *Pichia* or *Lindnera*). Preferably, the yeast strain used to prepare the extract belongs to the genus *Saccharomyces* and more particularly to the species *Saccharomyces cerevisiae*.

The 5'-ribonucleotide-rich yeast extract according to the invention can be obtained by processes known to the skilled person, for instance those described in the reference work "Yeast Technology" by G. Reed and T. W. Nagodawithana, $2^{nd}$ edition (Van Nostrand Reinhold, ISBN 0-442-31892-8) pages 382 to 385. In particular, it is known to prepare 5'-nucleotide-rich yeast extracts by enzymatic hydrolysis of yeasts in the presence of 5'-phosphodiesterase with deactivation of endogenous yeast phosphatases and nucleases. Yeast extracts containing the following 5'-ribonucleotides are thus obtained: 5'-GMP, 5'-UMP, 5'-CMP and 5'-AMP.

Among the known suitable processes for producing 5'-ribonucleotide-rich yeast derivatives, mention may also be made of the following: the U.S. Pat. No. 4,810,509 describes a process for producing 5'-nucleotide-rich yeast extract comprising (1) a step of heating a yeast suspension to between 55° C. and 70° C., (2) a step of autolysis of yeast cells at pH 8 to 10, (3) adjusting the pH of the autolyzed yeast suspension to between 5 and 7, (4) a step of heating this suspension to 90° C. or higher, (5) removing insoluble material from this heated suspension and (6) recovering the yeast extract containing 5'-nucleotides.

The process according to EP-A-0299078 consists in heating a yeast suspension containing a large amount of RNA to between 80° C. and 120° C. (destruction of ribonucleases), then extracting the RNA with an alkaline treatment and cleaving said RNA into 5'-nucleotides by the action of a 5'-phosphodiesterase.

The process according to WO02/067959 consists in preparing a yeast derivative by autolysis performed at a temperature above 35° C., for example between 35-70° C., preferably between 50-60° C. The yeasts are preferably hydrolyzed, during or after autolysis, with one or more proteases. Optionally, the product may be centrifuged and an additional step of ultrafiltration of the supernatant may also be performed.

The skilled person can therefore adapt the known processes so as to obtain a yeast extract comprising from 25 to 55 wt % 5'-ribonucleotides, including 5 to 20 wt % 5'-AMP and 5 to 20 wt % 5'-GMP in a 5'-AMP/5'-GMP ratio of between 0.85 and 1.25.

The skilled person also knows that a yeast extract comprising from 25 to 55 wt % ribonucleotides, including 5 to 20 wt % 5'-AMP and 5 to 20 wt % 5'-GMP, can be obtained by adding isolated or chemically synthesized 5'-ribonucleotides to a yeast extract comprising less than 25 wt % 5'-ribonucleotides. These yeast extracts are also part of the present invention. Those obtained by adding chemically synthesized 5'-ribonucleotides are not necessarily preferred because the products prepared from such yeast extracts must be labeled as containing a chemical additive.

The yeast extract according to the invention is therefore naturally rich in 5'-ribonucleotides and/or can be enriched by adding a quantity of 5'-ribonucleotides, said 5'-ribonucleotides being preferably obtained from yeast.

In the context of the present invention, the term "5'-ribonucleotides" refers to 5'-nucleotides themselves as well as hydrates thereof and other physiologically acceptable forms such as the disodium heptahydrate form. In particular, the 5'-ribonucleotides according to the invention are guanosine 5'-monophosphate (5'-GMP), adenosine 5'-monophosphate (5'-AMP), uridine 5'-monophosphate (5'-UMP) or cytidine 5'-monophosphate (5'-CMP), and inosine 5'-monophosphate (5'-IMP). Inosine 5'-monophosphate (5'-IMP) can notably be obtained by converting 5'-AMP with the enzyme 5'-adenylate deaminase (AMP deaminase).

According to a particularly preferred embodiment, the 5'-ribonucleotides do not include inosine 5'-monophosphate (5'-IMP). According to this embodiment, the yeast extract according to the invention is therefore free of 5'-IMP.

"5'-Ribonucleotide-rich yeast extract" means a yeast extract which comprises from 25 to 55 wt % 5'-ribonucleotides based on the dry weight of the yeast extract and calculated taking into account the disodium heptahydrate form. Preferably, the yeast extract comprises from 30 to 55 wt % 5'-ribonucleotides based on the dry weight of the yeast extract and most particularly from 35 to 55 wt % 5'-ribonucleotides based on the dry weight of the yeast extract.

Of the 25 to 55 wt % 5'-ribonucleotides, 5 to 20 wt % are 5'-AMP and 5 to 20 wt % are 5'-GMP. Preferably, of the 25 to 55 wt % 5'-ribonucleotides, 8 to 16 wt % are 5'-AMP and 8 to 16 wt % are 5'-GMP, and more preferably 9 to 14 wt % are 5'-AMP and 9 to 14 wt % are 5'-GMP.

Particularly advantageously, the yeast extract comprises from 40 to 55 wt % 5'-ribonucleotides, of which about 10 wt % are 5'-AMP and about 10 wt % are 5'-GMP. The yeast extract according to the invention also comprises less than 15 wt % 5'-CMP, preferably less than 12 wt % 5'-CMP, and most particularly less than 9 wt % 5'-CMP. The weight percentages are also expressed in relation to the dry weight of the yeast extract and are calculated taking into account the disodium heptahydrate form of the 5'-ribonucleotides.

In the yeast extract according to the invention, the 5'-AMP/5'-GMP ratio is 0.85 to 1.25. Preferably, the 5'-AMP/5'-GMP ratio is 0.90 to 1.15, preferably 0.95 to 1.10, more preferably 0.98 to 1.05, and most particularly the 5'-AMP/5'-GMP ratio is about 1.00.

The yeast extract according to the invention also has a free amino acid content of 0% to 20%, preferably of 1% to 10%, and a total amino acid content of 25% to 55%, and preferably of 35% to 45%.

The yeast extract according to the invention may be in the forms known to the skilled person. Preferably, the yeast extract is in the form of a dry extract.

According to a particular embodiment, the yeast extract according to the invention may be in powder form or in liquid form. Preferably, the yeast extract is in powder form.

According to another particular embodiment, the yeast extract according to the invention may be diluted in a physiologically acceptable carrier or excipient. A physiologically acceptable carrier or excipient is an aromatically neutral carrier or excipient suitable for administration to humans. Examples of physiologically acceptable carriers or excipients include maltodextrins, triacetin, propylene glycol, vegetable glycerin, glycerol, soluble fibers, yeast derivatives such as yeast extracts, bark and autolysates, or fats such as palm oil.

Another subject matter of the invention relates to the use of a yeast extract as defined above for the masking of bitter and sour tastes and of undesirable sweetener, protein and metallic notes in a product.

Within the meaning of the present invention, the product may also be a food, pharmaceutical or nutraceutical product or an aromatic preparation.

The yeast extract used according to the invention comprises from 25 to 55 wt % 5'-ribonucleotides based on the dry weight of the yeast extract. Preferably, the yeast extract comprises from 30 to 55 wt % 5'-ribonucleotides and most particularly from 35 to 55 wt % 5'-ribonucleotides based on the dry weight of the yeast extract.

Of the 25 to 55 wt % 5'-ribonucleotides, 5 to 20 wt % are 5'-AMP and 5 to 20 wt % are 5'-GMP. Preferably, of the 25 to 55 wt % 5'-ribonucleotides, 8 to 16 wt % are 5'-AMP and 8 to 16 wt % are 5'-GMP, and more preferably 9 to 14 wt % are 5'-AMP and 9 to 14 wt % are 5'-GMP.

Particularly advantageously, the yeast extract comprises from 40 to 55 wt % 5'-ribonucleotides, of which about 10 wt % are 5'-AMP and about 10 wt % are 5'-GMP.

In the yeast extract according to the invention, the 5'-AMP/5'-GMP ratio is 0.85 to 1.25. Preferably, the 5'-AMP/5'-GMP ratio is 0.90 to 1.15, preferably 0.95 to 1.10, more preferably 0.98 to 1.05, and most particularly the 5'-AMP/5'-GMP ratio is about 1.00.

The yeast extract used according to the invention also comprises less than 15 wt % 5'-CMP, preferably less than 12 wt % 5'-CMP, and most particularly less than 9 wt % 5'-CMP, the weight percentages also being expressed in relation to the dry weight of the yeast extract.

According to a particularly preferred embodiment, the yeast extract according to the invention is free of 5'-IMP.

The yeast extract according to the invention also has a free amino acid content of 0% to 20%, preferably of 1% to 10%, and a total amino acid content of 25% to 55%, and preferably of 35% to 45%.

The amounts of yeast extract present in the food product may be from 10 ppm to 1000 ppm. Preferably, the amounts of yeast extract are from 10 ppm to 500 ppm, preferably from 50 ppm to 200 ppm, and most particularly about 100 ppm. Surprisingly, when the amount of yeast extract exceeds 1000 ppm, the yeast extract no longer produces the different masks and, on the contrary, the taste and the undesirable notes are increased.

According to a particular embodiment, the yeast extract used according to the invention may be in powder form or in liquid form. Preferably, the yeast extract is in powder form.

According to another particular embodiment, the yeast extract used according to the invention may be diluted in a physiologically acceptable carrier or excipient. A physiologically acceptable carrier or excipient is an aromatically neutral carrier or excipient suitable for administration to humans. Examples of physiologically acceptable carriers or excipients include maltodextrins, triacetin, propylene glycol, vegetable glycerin, glycerol, soluble fibers, yeast derivatives such as yeast extracts, bark and autolysates, or fats such as palm oil.

Specifically, the use of a yeast extract according to the invention allows the masking of bitter and sour tastes and of undesirable sweetener, protein and metallic notes in a food product or a pharmaceutical product. Thus, the yeast extract provides several masks, contrary to what was known until now.

The use according to the invention is also particularly advantageous in that the yeast extract, when incorporated into the food or pharmaceutical product in the recommended amounts, does not produce the broth note, aromatic note or umami taste generally characteristic of yeast extracts.

As mentioned above, the food product may be considered as any substance providing nutrition for a living being, and particularly for a human being, and may be in either solid or liquid form. By way of example, the food product may be a prepared dish, a jam, a fermented drink such as wine or beer, an energy drink or a protein drink for sport.

Similarly, "pharmaceutical product" refers to any pharmaceutical substance intended to be ingested by a human being, such as a drug.

The notion of masking in a product refers to the fact that the presence of the yeast extracts according to the invention in said product reduces or even completely eliminates undesirable tastes and undesirable notes. The masking according to invention is therefore understood as the absence of said tastes and notes, or at least the reduction thereof. The absence or reduction in undesirable tastes and undesirable notes is demonstrated by human sensory perception since, to date, other methods, such as the use of an electronic tongue, do not allow fine detection of a particular masking. Indeed, current detection methods are not sufficiently representative of the human perception mechanism, which depends on a multitude of factors, some of which are not simply physiological.

Another subject matter of the invention relates to a process for masking bitter and sour tastes and undesirable sweetener, protein and metallic notes in a product.

The masking process according to the invention comprises the following steps:
  providing a yeast extract as defined above,
  incorporating said yeast extract into a product.

The process according to the invention makes it possible to mask bitter and sour tastes and undesirable sweetener, protein and metallic notes in a product. For example, the product may be a food, pharmaceutical or nutraceutical product or an aromatic preparation. Exemplary food products include a prepared dish, a jam, a fermented drink such as wine or beer, an energy drink or a protein drink for sport. An exemplary pharmaceutical product is a drug.

According to the process of the invention, the yeast extract provided comprises notably from 25 to 55 wt % 5'-ribonucleotides, including 5 to 20 wt % adenosine 5'-monophosphate (5'-AMP) and 5 to 20 wt % guanosine 5'-monophosphate (5'-GMP) in a 5'-AMP/5'-GMP ratio ranging from 0.85 to 1.25.

The incorporation step is a step known to the skilled person and consists notably in applying and/or mixing the yeast extract in the product. This incorporation step may therefore be carried out both during and after the manufacture of said product and may also be carried at high or low temperature.

The amounts of yeast extract to be incorporated may be from 10 ppm to 1000 ppm. Preferably, the amounts of yeast extract to be incorporated are from 10 ppm to 500 ppm, more preferably from 50 ppm to 200 ppm, and most particularly about 100 ppm.

Surprisingly, when the amount of yeast extract to be incorporated exceeds 1000 ppm, the masking of bitter and sour tastes is no longer present and, conversely, said tastes are more pronounced in the product.

According to a particular embodiment, the yeast extract provided according to the first step of the process of the invention may be in powder form or in liquid form. Preferably, the yeast extract is in powder form.

According to another particular embodiment, the yeast extract provided according to the first step of the process of the invention may be diluted in a physiologically acceptable carrier or excipient. A physiologically acceptable carrier or excipient is an aromatically neutral carrier or excipient suitable for administration to humans. Examples of physiologically acceptable carriers or excipients include maltodextrins, triacetin, propylene glycol, vegetable glycerin, glycerol, soluble fibers, yeast derivatives such as yeast extracts, bark and autolysates, or fats such as palm oil.

The invention will be better understood with the help of the following examples, which are intended to be purely illustrative and in no way limit the scope of the invention.

EXAMPLES

A comparative organoleptic study was conducted by a panel of 7 experts on products optionally prepared from a yeast extract according to the invention.

Example 1: Masking of Undesirable Sweetener Notes

In this example, the masking of undesirable sweetener notes by a yeast extract according to the invention was demonstrated in a jam and in an iced tea.

Yeast Extracts:

Two yeast extracts were prepared. The first (EXL1) is a 5'-ribonucleotide-rich yeast extract according to the invention comprising between 10 and 15 wt % 5'-AMP and 5'-GMP in a 5'-AMP/5'-GMP ratio of 0.98. EXL1 is prepared from a yeast strain of the species Saccharomyces cerevisiae. The yeast strains are first subjected to heat shock at a temperature above 75° C. before an enzyme, phosphodiesterase, is added at a pH between 4.5 and 7.5. The strains are then subjected to hydrolysis for 8 to 24 hours at a temperature between 40 and 70° C., then a separation step is performed. The supernatant is then recovered, concentrated and dried to obtain extract EXL1 according to the invention.

The second extract (EXL2) is a commercial yeast extract sold by the Applicant under the name Springer®2020. This extract is different from the yeast extracts according to the invention in that it notably does not contain 5'-AMP; it is thus used for purposes of comparison.

The amounts of the different 5'-ribonucleotides in the yeast extracts are listed in Table 1 below:

TABLE 1

| EXL 1 | EXL 2 (comparative) |
| --- | --- |
| 50.9 wt % 5'-ribonucleotides, including: | 50.9 wt % 5'-ribonucleotides, including: |
| 10 wt % 5'-AMP | 10.1 wt % 5'-IMP |
| 10.1 wt % 5'-GMP | 10.2 wt % 5'-GMP |

Food Products Used to Demonstrate Masking:
  Product 1 (control): Gerblé® commercial apricot jam containing 0.03-0.04% sucralose as sweetener. The percentages are expressed in relation to the total weight of the jam.
  Product 2 (comparative): Gerblé® commercial apricot jam uniformly mixed with 100 ppm EXL2.

Product 3: Gerblé® commercial apricot jam uniformly mixed with 100 ppm EXL1.

Product 4: Gerblé® commercial apricot jam uniformly mixed with 2000 ppm EXL1.

Product 5 (control): *Stevia*-based iced tea containing 0.035% steviosides as sweetener. The percentages are expressed in relation to the total weight of the drink.

Product 6 (comparative): *Stevia*-based iced tea uniformly mixed with 100 ppm EXL2.

Product 7: *Stevia*-based iced tea uniformly mixed with 100 ppm EXL1.

The compositions of products 5, 6 and 7 are shown in Table 2 below:

TABLE 2

| Iced tea | Product 5 | Product 6 | Product 7 |
| --- | --- | --- | --- |
| Water | 99.78 | 99.77 | 99.77 |
| Citric acid | 0.15 | 0.15 | 0.15 |
| Green tea extract | 0.02 | 0.02 | 0.02 |
| MANE M57337 peach flavor | 0.01 | 0.01 | 0.01 |
| Stevia 97% Reb A | 0.035 | 0.035 | 0.035 |
| EXL 1 | | | 0.0100 |
| EXL 2 | | 0.0100 | |
| TOTAL | 100.00 | 100.00 | 100.00 |

The products were then submitted to a panel of experts for comparative organoleptic analysis. Each expert tasted the control product for a blind comparison with the products containing the yeast extracts. For the products containing the yeast extracts, the panel members were also asked to determine the absence or presence of aromatic notes of yeast. The results are as follows:

Product 1: The apricot aroma is pronounced, with a sourness in the mouth and a sweetener note.

Product 2: The apricot aroma is still as pronounced, less sweet taste, the sourness in the mouth is more pronounced than product 1, the sweetener note is less pronounced but still present. The panel experts identify aromatic notes of yeast.

Product 3: The apricot aroma is more pronounced, as is the sweet taste, and no sweetener note. The panel experts note the absence of aromatic notes of yeast.

Product 4: The apricot aroma is still as pronounced, with a sweetener note. The panel experts also identify aromatic notes of yeast.

Product 5: Pronounced sweet taste, presence of fruity aromas, presence of a sweetener note that also persists after swallowing.

Product 6: Less pronounced sweet taste, the sweetener note is less pronounced but still present. The panel experts identify aromatic notes of yeast in the iced tea.

Product 7: Less pronounced sweet taste and slight sourness. No sweetener note. The panel experts do not identify any aromatic notes of yeast in the iced tea.

By the absence of detection of sweetener notes by the panel of experts, this example clearly demonstrates the masking capacity of the yeast extract according to the invention, said extract also being advantageous in that no aromatic notes of yeast are present in the food product. Similarly, comparative product 4 demonstrates the importance of the proportion of the yeast extract according to the invention in obtaining the masking of sweetener notes. Indeed, said masking cannot be obtained when the proportion is too high.

Example 2: Masking of Bitter Taste

In this example, the masking of bitter aftertaste by a yeast extract according to the invention was demonstrated in a caramel sauce.

Yeast Extracts:

Two yeast extracts were prepared and used. These are the same extracts (EXL1 and EXL2) as in Example 1 above.

Food Products Used to Demonstrate Masking:

Product 8 (control): Vahiné® commercial caramel sauce.

Product 9 (comparative): Vahiné® commercial caramel sauce uniformly mixed with 100 ppm EXL2.

Product 10: Vahiné® commercial caramel sauce uniformly mixed with 100 ppm EXL1.

Following the same protocol as in Example 1, each product was submitted to a panel of experts for comparative organoleptic analysis and the results are as follows:

Product 8: Pronounced caramel aroma, presence of a burnt aroma, very pronounced sweet taste and presence of bitter taste.

Product 9: Caramel aroma still pronounced relative to product 8, sweet taste still as pronounced, similar presence of a bitter taste. In addition, the panel experts identify aromatic notes of yeast.

Product 10: Caramel aroma still pronounced and sweet taste more pronounced in the mouth than product 8. On the other hand, the experts note the absence of bitter taste and the absence of aromatic notes of yeast.

The study by the panel of experts thus demonstrates that the yeast extract according to the invention produces a product with a more pronounced sweet taste in the mouth than the original product while masking the bitter taste and without generating aromatic notes of yeast in the food product.

Example 3: Masking of Undesirable Protein Notes (a) Pea Protein Solution

In this example, the masking of protein notes by a yeast extract according to the invention was demonstrated in a protein water.

Yeast Extracts:

Two yeast extracts were prepared. These are the same extracts (EXL1 and EXL2) as in Example 1 above.

Food Products Used to Demonstrate Masking:

Product 11 (control): 3% solution of Peatex® pea proteins in water.

Product 12 (comparative): 3% solution of Peatex® pea proteins in water uniformly mixed with 50 ppm EXL 2.

Product 13: 3% solution of Peatex® pea proteins in water uniformly mixed with 50 ppm EXL 1.

Following the same protocol as in the previous examples, each product was submitted to the panel of experts for comparative organoleptic analysis and the results are as follows:

Product 11: Bitter solution, presence of an undesirable pea protein note and an undesirable metallic note.

Product 12: Solution still as bitter, the metallic note as pronounced and a very slight reduction in the undesirable pea protein note. The panel experts identify aromatic notes of yeast.

Product 13: Solution less bitter than the control, less pronounced undesirable metallic note and substantial reduction in undesirable pea protein note. The panel experts note the absence of an aromatic note of yeast.

The results of the organoleptic study thus demonstrate the protein note-masking properties. Indeed, adding yeast extracts according to the invention (EXL1) leads to a clear reduction in undesirable protein notes but also, advantageously, a reduction in the bitter taste, and without however generating an aromatic note of yeast.

(b) "Chicken in Tomato Sauce" Vegan Product.

The masking of protein notes by a yeast extract according to the invention was also demonstrated in a "chicken in tomato sauce" vegan product.

Yeast Extracts:

Two yeast extracts were prepared. These are the same extracts (EXL1 and EXL2) as in Example 1 above.

Food Products Used to Demonstrate Masking:
  Product 14 (control): Tinned prepared dish based on Trutex® 1501 textured wheat protein (MGP Ingredients).
  Product 15: Tinned prepared dish based on Trutex® 1501 textured wheat protein uniformly mixed with 100 ppm EXL 1.

The compositions of products 14 and 15 are shown in Table 3 below:

TABLE 3

| Tinned prepared dish based on textured wheat protein | Product 14 | Product 15 |
| --- | --- | --- |
| Water | 85.85 | 85.84 |
| Trutex 1501 (hydrolyzed wheat protein) | 7.00 | 7.00 |
| Tomato paste | 2.00 | 2.00 |
| Sugar | 1.00 | 1.00 |
| Maltodextrin | 1.00 | 1.00 |
| Sunflower oil | 1.00 | 1.00 |
| Corn starch | 0.80 | 0.80 |
| Salt | 0.60 | 0.60 |
| Grilled onion powder | 0.50 | 0.50 |
| Xanthan gum | 0.10 | 0.10 |
| Laurel powder | 0.10 | 0.10 |
| Mixed herbs | 0.05 | 0.05 |
| EXL1 |  | 0.01 |
| TOTAL | 100.00 | 100.00 |

The compositions were tinned and sterilized for 12 minutes at 121° C.

Following the same protocol as in the previous examples, each product was submitted to the panel of experts for comparative organoleptic analysis and the results are as follows:
  Product 14: Presence of an undesirable vegetable protein note and an undesirable metallic note.
  Product 15: Substantial reduction in the vegetable protein afternote. The panel experts note the absence of an aromatic note of yeast.

This organoleptic study thus once again demonstrates the masking properties of the extract according to the invention. Indeed, adding yeast extracts according to the invention (EXL1) results in a substantial reduction in the vegetable protein aromatic note and the undesirable metallic note without however generating an aromatic note of yeast.

Example 4: Masking of Undesirable Metallic Notes

In this example, the masking of metallic notes by a yeast extract according to the invention was detected in a high potassium chloride (KCl) soup.

Yeast Extracts:

Two yeast extracts were prepared. These are the same extracts (EXL1 and EXL2) as in Example 1 above.

Food Products Used to Demonstrate Masking:
  Product 16 (control): Campbell's® commercial tomato soup containing 0.25% KCl.
  Product 17 (comparative): Campbell's® commercial tomato soup uniformly mixed with 100 ppm EXL 2.
  Product 18: Campbell's® commercial tomato soup uniformly mixed with 100 ppm EXL 1.

Following the same protocol as in the previous examples, each product was submitted to the panel experts for comparative organoleptic analysis and the results are as follows:
  Product 16: Pronounced tomato aroma, presence of a sweet taste, presence of a slight bitter taste, and very pronounced presence of an undesirable metallic note notably due to potassium chloride.
  Product 17: The tomato aroma is as pronounced as product 14, the sweet taste is slightly more pronounced, the bitter taste and the undesirable metallic note are still pronounced. The panel experts identify aromatic notes of yeast.
  Product 18: The bitter taste is less pronounced. The undesirable metallic note is substantially reduced compared with product 14. The panel experts note the absence of an aromatic note of yeast.

The results thus show the beneficial effect of the yeast extract according to the invention on the masking of metallic notes without always inducing aromatic notes of yeast in the resulting product.

Example 5: Masking of Sour Taste

In this example, the masking of the "sour" note by a yeast extract according to the invention was demonstrated in a Bonne Maman® brand jam.

Yeast Extract:

Two yeast extracts were prepared. These are the same extracts (EXL1 and EXL2) as in Example 1 above.

Food Products Used to Demonstrate Masking:
  Product 19 (control): Bonne Maman® brand commercial strawberry jam.
  Product 20 (comparative): Bonne Maman® brand commercial strawberry jam uniformly mixed with 100 ppm EXL 2.
  Product 21: Bonne Maman® brand commercial strawberry jam uniformly mixed with 100 ppm EXL 1.

The products were then submitted to a panel of experts for comparative organoleptic analysis. Each expert tasted the control product for comparison with the product containing the yeast extracts. Panel members were also asked to determine the absence or presence of aromatic notes of yeast. The results are as follows:
  Product 19: The strawberry aroma is pronounced, presence of a sweet taste in the mouth and above all presence of peak of sour taste in the product.
  Product 20: The sweet taste is more pronounced, the strawberry aroma is less present and the sour taste is still as present. The panel experts identify the presence of slight aromatic notes of yeast on aftertaste.
  Product 21: The sweet taste is slightly more pronounced but above all more prolonged over time, while the sour taste is absent from the product. The experts do not identify any aromatic notes of yeast in the product.

The results thus show the beneficial effect of the yeast extract according to the invention on masking sour taste without inducing aromatic notes of yeast in the food product.

Examples 1 to 5 were reproduced while replacing yeast extract EXL1 with either yeast extract EXL3 or yeast extract EXL4, said extracts EXL3 and EXL4 also being extracts according to the invention and whose compositions are listed in Table 4 below:

TABLE 4

| EXL 3 | EXL 4 |
|---|---|
| 44.8 wt % 5'-ribonucleotides, including: | 39.91 wt % 5'-ribonucleotides, including: |
| 11.9 wt % 5'-AMP | 10.13 wt % 5'-AMP |
| 11.8 wt % 5'-GMP | 11.57 wt % 5'-GMP |

The results of the organoleptic studies conducted by the same panel of experts are the same as those obtained with yeast extract EXL1, and thus demonstrate once again the beneficial effects of the yeast extracts according to the invention on the masking of bitter and sour tastes and of undesirable sweetener, protein and metallic notes.

Example 6: Masking Effect of a Yeast Extract According to the Invention Mixed with an Aromatically Neutral Carrier The aromatically neutral carrier used for this example is the maltodextrin Glucidex® 12, sold by Roquette.

Yeast extract EXL 1, described above, was mixed with this maltodextrin to obtain a final mixture having 10 wt % 5'-AMP and 5'-GMP and a 5'-AMP/5'-GMP ratio of 0.98. The mixture of maltodextrin and extract EXL 1 thus obtained was then added to the products listed below and described in the previous examples, namely:

Product 5: *Stevia*-based iced tea comprising 0.035% steviosides as sweetener. The percentages are expressed in relation to the total weight of the drink, Product 11: 3% solution of Peatex® pea proteins in water, Product 16: Campbell's® commercial tomato soup containing 0.25% KCl, Product 19: Bonne Maman® brand commercial strawberry jam.

The amounts of the mixture of maltodextrins and extract EXL 1 added are 100 ppm for products 5, 16 and 19 and 50 ppm for product 11.

The products obtained were then submitted to the panel of experts for a comparative organoleptic analysis.

The masking effects of the mixture of maltodextrin and extract EXL 1 in products 5, 11, 16 and 19 were compared with those obtained in the same products but in the presence of yeast extract EXL 1 alone (products 7, 13, 18 and 21).

The results show that adding maltodextrin to yeast extract EXL1 does not alter the masking properties with respect to sour taste and to undesirable sweetener, protein and metallic notes.

The invention claimed is:

1. A 5'-ribonucleotide-rich yeast extract comprising from 25 to 55 wt % 5'-ribonucleotides, wherein the yeast extract comprises 5 to 20 wt % 5'-AMP and 5 to 20 wt % 5'-GMP, in a 5'-AMP/5'-GMP ratio of between 0.85 and 1.25, the weight percentages being based on the dry weight of the yeast extract.

2. The yeast extract as claimed in claim 1, wherein the yeast extract is obtained from a yeast strain of the species *Saccharomyces cerevisiae*.

3. The yeast extract as claimed in claim 1, wherein the yeast extract is free of 5'-IMP.

4. The yeast extract as claimed in claim 1, wherein the yeast extract comprises from 35 to 55 wt % 5'-ribonucleotides.

5. The yeast extract as claimed in claim 1, wherein the yeast extract comprises from 8 to 16 wt % 5'-AMP and 8 to 16 wt % 5'-GMP.

6. The yeast extract as claimed in claim 5, wherein yeast extract comprises from 9 to 14 wt % 5'-AMP and 9 to 14 wt % 5'-GMP.

7. The yeast extract as claimed in claim 1, wherein the yeast extract comprises a free amino acid content of 0% to 20% and a total amino acid content of 25% to 55%.

8. A process for masking bitter and sour tastes and undesirable sweetener, protein and metallic notes in a product comprising the incorporation of 10 to 1000 ppm of a yeast extract as defined according to claim 1 into said product.

9. The masking process as claimed in claim 8, wherein the incorporation of the yeast extract into the product is carried out during or after the manufacture of said product.

10. The masking process as claimed in claim 8, wherein the product is a food, pharmaceutical or nutraceutical product or an aromatic preparation.

11. The masking process as claimed in claim 8, wherein the yeast extract is present in the food product in an amount between 50 ppm and 200 ppm.

12. The yeast extract as claimed in claim 1, wherein the 5'-AMP/5'-GMP ratio is from 0.90 to 1.15.

13. The yeast extract as claimed in claim 1, wherein the 5'-AMP/5'-GMP ratio is from 0.95 to 1.10.

14. The yeast extract as claimed in claim 1, wherein the 5'-AMP/5'-GMP ratio is from 0.98 to 1.05.

15. The yeast extract as claimed in claim 1, wherein the 5'-AMP/5'-GMP ratio is about 1.

* * * * *